US011117870B2

(12) United States Patent
Kim et al.

(10) Patent No.: US 11,117,870 B2
(45) Date of Patent: Sep. 14, 2021

(54) COMPOUNDS, COMPOSITIONS, AND METHODS FOR TREATING DISEASES

(71) Applicant: Drexel University, Philadelphia, PA (US)

(72) Inventors: Felix Kim, Philadelphia, PA (US); Joseph Salvino, Chester Springs, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 16/761,161

(22) PCT Filed: Nov. 1, 2018

(86) PCT No.: PCT/US2018/058674
§ 371 (c)(1),
(2) Date: May 1, 2020

(87) PCT Pub. No.: WO2019/089902
PCT Pub. Date: May 9, 2019

(65) Prior Publication Data
US 2020/0339519 A1 Oct. 29, 2020

Related U.S. Application Data

(60) Provisional application No. 62/580,089, filed on Nov. 1, 2017.

(51) Int. Cl.
*C07D 239/42* (2006.01)
*A61K 45/06* (2006.01)

(52) U.S. Cl.
CPC ............ *C07D 239/42* (2013.01); *A61K 45/06* (2013.01)

(58) Field of Classification Search
None
See application file for complete search history.

(56) References Cited

U.S. PATENT DOCUMENTS

| 3,723,463 A | 3/1973 | Bernstein et al. |
| 3,855,242 A | 12/1974 | Chapman et al. |
| 4,680,300 A | 7/1987 | Nelson et al. |
| 4,713,382 A | 12/1987 | Pascal |
| 4,921,856 A | 5/1990 | Schickaneder et al. |
| 4,921,939 A | 5/1990 | Nofre et al. |
| 4,946,842 A | 8/1990 | Coates et al. |
| 4,968,683 A | 11/1990 | Moersdorf et al. |
| 5,006,523 A | 4/1991 | Atwal |
| 5,116,838 A | 5/1992 | Ishikawa et al. |
| 5,385,946 A | 1/1995 | Keana et al. |
| 5,482,948 A | 1/1996 | Soyka et al. |
| 5,741,796 A | 4/1998 | Hartman et al. |
| 5,837,718 A | 11/1998 | Timmerman et al. |
| 6,001,836 A | 12/1999 | Poindexter et al. |
| 6,060,484 A | 5/2000 | Fritz et al. |
| 6,143,791 A | 11/2000 | Goldin et al. |
| 6,147,098 A | 11/2000 | Mogensen et al. |
| 6,288,123 B1 | 9/2001 | Goldin et al. |
| 6,646,137 B1 | 11/2003 | Anderson et al. |
| 6,875,759 B1 | 4/2005 | Lipkowski et al. |
| 6,881,753 B2 | 4/2005 | Lloyd et al. |
| 7,001,904 B1 | 2/2006 | Poyser et al. |
| 7,138,530 B2 | 11/2006 | Subasinghe et al. |
| 7,199,129 B2 | 4/2007 | Jackson et al. |
| 7,304,086 B2 | 12/2007 | Schilling et al. |
| 7,351,743 B1 | 4/2008 | Goldin et al. |
| 7,371,871 B2 | 5/2008 | Schilling et al. |
| 7,439,256 B2 | 10/2008 | Castelhano et al. |
| 7,582,656 B2 | 9/2009 | Roche et al. |
| 7,728,005 B2 | 6/2010 | Okuzumi et al. |
| 7,732,162 B2 | 6/2010 | Hoffman et al. |
| 7,790,719 B2 | 9/2010 | Vos et al. |
| 7,863,465 B2 | 1/2011 | Balkovec et al. |
| 7,872,005 B2 | 1/2011 | Sun et al. |
| 7,956,219 B2 | 6/2011 | Ede et al. |
| 8,168,787 B2 | 5/2012 | Falchi et al. |
| 8,227,498 B2 | 7/2012 | Buchholz et al. |
| 8,324,258 B2 | 12/2012 | Glick et al. |
| 8,338,120 B2 | 12/2012 | Schilling et al. |
| 8,409,837 B2 | 4/2013 | Schilling et al. |
| 8,497,307 B2 | 7/2013 | Glick et al. |
| 8,648,111 B2 | 2/2014 | Kim et al. |
| 9,133,110 B2 | 9/2015 | Kim et al. |
| 9,388,126 B2 | 7/2016 | Kim et al. |

(Continued)

FOREIGN PATENT DOCUMENTS

| EP | 241395 A2 | 10/1987 |
| WO | 9014067 A2 | 11/1990 |

(Continued)

OTHER PUBLICATIONS

European Search Report issued for European Patent Application No. 13819583.9 dated Nov. 30, 2015.
PCT International Search Report issued for PCT/US2013/051110 dated Feb. 28, 2014.
International Search Report and Written Opinion dated Jan. 18, 2019 for International Application No. PCT/US2018/58674.
Akhter, et al., "A change of in vivo characteristics depending on specific activity of radioiodinated (+)-2-[4-(4-iodophenyl)piperidino]cyclohexanol [(+)-pIV] as a ligand for sigma receptor imaging", Nucl. Med. Biol. 35, 2008, 29-34.

(Continued)

*Primary Examiner* — Craig D Ricci
(74) *Attorney, Agent, or Firm* — Saul Ewing Arnstein & Lehr LLP; Kathryn Doyle; Domingos J. Silva

(57) ABSTRACT

The present application is directed, in part, to compounds, and/or pharmaceutically acceptable salts or solvates thereof, and/or pharmaceutical compositions thereof, for modulating the activity of Sigma I receptor. The present application is further directed, in part, to methods for treating and/or preventing cancer using compounds disclosed herein, and/or pharmaceutically acceptable salts or solvates thereof, and/or pharmaceutical compositions thereof.

9 Claims, No Drawings

(56) References Cited

U.S. PATENT DOCUMENTS

| | | | |
|---|---|---|---|
| 9,889,102 | B2 | 2/2018 | Kim et al. |
| 2005/0192314 | A1 | 9/2005 | Mehta et al. |
| 2007/0191366 | A1 | 8/2007 | Hoffmann et al. |
| 2008/0125424 | A1 | 5/2008 | DePrez et al. |
| 2008/0255143 | A1 | 10/2008 | Heerding et al. |
| 2010/0184787 | A1 | 7/2010 | Amberg et al. |
| 2014/0154182 | A1 | 6/2014 | Klein et al. |

FOREIGN PATENT DOCUMENTS

| | | |
|---|---|---|
| WO | 9118868 A1 | 12/1991 |
| WO | 9520950 A1 | 8/1995 |
| WO | 9844797 A1 | 10/1998 |
| WO | 0009115 A1 | 2/2000 |
| WO | 0009116 A1 | 2/2000 |
| WO | 02094265 A1 | 11/2002 |
| WO | 03068738 A1 | 8/2003 |
| WO | 2005048953 A3 | 2/2006 |
| WO | 2008034891 A2 | 3/2008 |
| WO | 2011060394 A1 | 5/2011 |
| WO | 2011060395 A1 | 5/2011 |
| WO | 2012165956 A1 | 12/2012 |
| WO | 2014015157 A3 | 4/2014 |

OTHER PUBLICATIONS

Aydar, et al., "The Sigma Receptor as a Ligand-Regulated Auxiliary Potassium Channel Subunit", Neuron 34:2002, 399-410.

Behensky, et al., "In Vitro Evaluation of Guanidine Analogs as Sigma Receptor Ligands for Potential Anti-Stroke Therapeutics", J. Pharmacol. Exp. Ther., 344:2013, 155-166.

Berthois, et al., "SR31747A is a sigma receptor ligand exhibiting antitumoural activity both in vitro and in vivo", Br. J. Cancer 88:2003, 438-446.

Boguszewski, et al., "Modular three-component solid-phase synthesis of unsymmetrical guanidines via resin capture of carbodiimides", J Comb Chem. 6(1), Jan.-Feb. 2004, 32-34.

Chou, et al., "Reversible inhibitor of p97, DBeQ, impairs both ubiquitin-dependent and autophagic protein clearance pathways", Proc Natl Acad Sci U S A., 108(12), Mar. 22, 2011, 4834-4839.

Dahmen, et al., "A novel solid-phase synthesis of highly diverse guanidines: reactions of primary amines attached to the T2 linker", Org Lett. 2(23), 2000, 3563-3565.

Ding, et al., "Linking of Autophagy to Ubiquitin-Proteasome System is Important for the Regulation of Endoplasmic Reticulum Stress and Cell Viability", American Journal of Pathology, 171(2), Aug. 2007, 513-524.

Fontanilla, et al., "The Hallucinogen N,N-Dimethyltryptamine (DMT) Is an Endogenous Sigma-1 Receptor Regulator", Science, 323, 2009, 934-937.

Hammoud, et al., "Direct guanidinylation of aryl and heteroaryl halides via copper-catalyzed cross-coupling reaction", J Org Chem. 77(1), 2012, 417-423.

Hanner, et al., "Purification, molecular cloning, and expression of the mammalian sigma1-binding site", Proc. Natl. Acad. Sci. U.S.A. 93:, 1996, 8072-8077.

Hayashi, et al., "Sigma-1 Receptors (Binding Sites) Form Raft-Like Microdomains and Target Lipid Droplets on the Endoplasmic Reticulum: Roles in Endoplasmic Reticulum Lipid Compartmentalization and Export", J. Pharmacol. Exp. Ther. 306, 2003, 718-725.

Hayashi, et al., "Sigma-1 Receptor Chaperones at the ERMitochondrion Interface Regulate Ca2+ Signaling and Cell Survival", Cell 131:2007, 596-610.

Kim, et al., "Inhibition of tumor cell growth by Sigma1 ligand mediated translational repression", Biochem Biophys Res Commun. 426(2), 2012, 177-182.

Mathew, et al., "Role of autophagy in cancer", Nat. Rev. Cancer, 7, 2007, 961-967.

Pal, et al., "Identification of Regions of the -1 Receptor Ligand Binding Site Using a Novel Photoprobe", Mol. Pharmacol. 72:2007, 3338-46.

Palmer, et al., "Sigma-1 Receptors Bind Cholesterol and Remodel Lipid Rafts in Breast Cancer Cell Lines", Cancer Res. 67, 2007, 11166-11175.

Partridge, et al., "The synthesis of NN'-disubstituted guanidines and some observations on the mechanism of the Tiemann reaction", J Pharm Pharmacol. 5(2)., 1953, 103-110.

Piergentili, et al., "Novel Highly Potent and Selective Receptor Antagonists Related to Spipethiane", J. Med. Chem. 53:1261-1269, 2010, 1261-1269.

Roh, et al., "Intrathecal injection of the sigma(1) receptor antagonist BD1047 blocks both mechanical allodynia and increases in spinal NR1 expression during the induction phase of rodent neuropathic pain", Anesthesiology. 109(5), 2008, 879-889.

Salvino, et al., "Novel small molecule guanidine Sigma1 inhibitors for advanced prostate cancer", Bioorg Med Chem Lett. 27(10), 2017, 2216-2220.

Smith, "Mono-Arylguanidines I. Alpha-Phenylguanidine", J. Am. Chem. Soc. 51, 1929, 476-479.

Spruce, et al., "Small molecule antagonists of the sigma-1 receptor cause selective release of the death program in tumor and self-reliant cells and inhibit tumor growth in vitro and in vivo", Cancer Research, 64(14), Jul. 14, 2004, 4875-4886.

Tsaytler, et al., "Selective Inhibition of a Regulatory Subunit of Protein Phosphatase 1 Restores Proteostasis", Science 332, Mar. 2, 2011, 91-94.

Tu, et al., "Fluorine-18-Labeled Benzamide Analogues for Imaging the Receptor Status of Solid Tumors with Positron Emission Tomography", J. Med. Chem. 50:2007, 3194-3204.

Vilner, et al., "Cytotoxic Effects of Sigma Ligands: Sigma Receptor-mediated Alterations in Cellular Morphology and Viability", J. Neurosci. 15:, 1995, 117-134.

Vilner, et al., "Sigma-1 and Sigma-2 Receptors Are Expressed in a Wide Variety of Human and Rodent Tumor Cell Lines", Cancer Res. 55: 1995, 408-413.

White, et al., "The Double-Edged Sword of Autophagy Modulation in Cancer", Clin. Cancer Res. 15:, 2009, 5308-5316.

COMPOUNDS, COMPOSITIONS, AND METHODS FOR TREATING DISEASES

CROSS REFERENCE TO RELATED APPLICATIONS

The present application is a 35 U.S.C. § 371 national phase application of, and claims priority to, International Application No. PCT/US2018/058674, filed Nov. 1, 2018, which claims priority under 35 U.S.C. § 119(e) to U.S. Provisional Patent Application No. 62/580,089, filed Nov. 1, 2017, all of which applications are hereby incorporated herein by reference in their entireties.

BACKGROUND OF THE INVENTION

Sigma receptors, first proposed 30 years ago (Martin et al., 1976, J. Pharmacol. Exp. Ther. 197:517-532), are distinct from classical opioid receptors (Su, 1982, J. Pharmacol. Exp. Ther. 223:284-290). Binding studies suggest at least two Sigma receptor subtypes, of which only the Sigma receptor (hereinafter "Sigma1") has been cloned. The identity of Sigma2 remains unclear (Hanner et al., 1996, Proc. Natl. Acad. Sci. U.S.A. 93:8072-8077; Vilner et al., 1995, Cancer Res. 55:408-413).

Sigma1 is highly conserved among mammals (greater than 80% amino acid identity), but shares no significant homology with any traditional receptor family or other mammalian protein (White et al., 2009, Clin. Cancer Res. 15:5308-5316; Mathew, et al., 2007, Nat. Rev. Cancer 7:961-967). Cloned Sigma1 is a 26 kilodalton integral membrane protein (Hanner et al., 1996, Proc. Natl. Acad. Sci. U.S.A. 93:8072-8077; Pal et al., 2007, Mol. Pharmacol. 72:921-933; Aydar et al., 2007, Neuron 34:399-410; Hayashi et al., 2007, Cell 131:596-610). It is found primarily in the ER, and can translocate to the plasma membrane, other organelles, and endoplasmic membrane microdomains (Hanner et al., 1996, Proc. Natl. Acad. Sci. U.S.A. 93:8072-8077; Aydar et al., 2007, Neuron 34:399-410; Hayashi et al., 2007, Cell 131:596-610; Hayashi et al., 2003, J. Pharmacol. Exp. Ther. 306:718-725; Palmer et al., 2007, Cancer Res. 67:11166-11175).

Sigma receptors are highly expressed in tumor cell lines, including prostate and breast adenocarcinoma (Vilner et al., 1995, Cancer Res. 55:408-413; Berthosis et al., 2003, Br. J. Cancer 88:438-446; Piergentili et al., J. Med. Chem. 53:1261-1269). Some Sigma ligands are reported as antitumor agents (Berthosis et al., 2003, Br. J. Cancer 88:438-446; Vilner et al., 1995, J. Neurosci. 15:117-134). Interestingly, putative Sigma antagonists, but not agonists, inhibit prostate carcinoma proliferation in vitro and inhibit tumor growth in tumor xenograft experiments (Berthosis et al., 2003, Br. J. Cancer 88:438-446; Spruce et al., 2004, Cancer Res. 64:4875-4886). Recent work has described Sigma ligand-induced cell death by lysosomal destabilization and oxidative stress.

There are numerous examples of clinically used compounds that bind Sigma1 with high affinity and thus are considered Sigma1 ligands. Examples of such ligands are haloperidol, which is a widely used antipsychotic that binds D2 receptors with similar affinity and whose anti-psychotic properties are primarily understood as D2 mediated (Seeman, et al., 1975, Science 188:1217-1219; Seeman et al., 1976, Nature 261:717-719), and the hallucinogen N,N-dimethyltryptamine, which is hypothesized to be an endogenous Sigma1 regulator (Fontanilla et al., 2009, Science 323:934-937).

Sigma receptors are highly attractive pharmacological targets for the treatment of various pathologies, such as neuropathic pain (de la Puente et al., 2009, Pain 145:294-303), depression (Skuza, 2003, Pol. J. Pharmacol. 55:923-934), cocaine abuse (Matsumoto et al., 2003, Eur. J. Pharmacol. 469:1-12), epilepsy (Lin et al., 1997, Med. Res. Rev. 17:537-572), psychosis (Rowley et al., 2001, J. Med. Chem. 44:477-501), and Alzheimer's and Parkinson's disease (Maurice et al., 1997, Prog. Neuro-Psychopharmacol. Biol. Psychiatry 21:69-102; Marrazzo et al., 2005, NeuroReport 16:1223-1226). Recent reports demonstrate a genetic link between the Sigma1 receptor gene (SIGMAR1) and Amyotrophic lateral sclerosis (ALS) (Al-Saif et al., 2011, Ann Neurol. 70(6):913-9), as well as Frontotemporal Lobar Degeneration (FTLD) (Luty et al., 2010, Ann Neurol. 2010 68(5):639-49). Moreover, Sigma1 antagonists and Sigma2 agonists can be useful as anticancer agents and selective tumor imaging agents (Akhter et al., 2008, Nucl. Med. Biol. 35:29-34; Tu et al., 2007, J. Med. Chem. 50:3194-3204).

Sigma1 can function as a molecular chaperone at the ER-mitochondrion interface at least in certain model cell lines (Hayashi & Su, 2007, Cell 131(3):596-610). However, the physiological role of Sigma receptors as well as their role in neurodegenerative disease and cancer remains unclear. In vitro, treatment with a Sigma antagonist results in apoptotic cell death following prolonged treatment, with Sigma ligand time-action and dose-response, depending on the Sigma antagonist and cell line (Berthosis et al., 2003, Br. J. Cancer 88:438-446; Piergentili et al., J. Med. Chem. 53:1261-1269; Spruce et al., 2004, Cancer Res. 64:4875-4886; Vilner et al., 1995, J. Neurosci. 15:117-134). Yet, a mechanistic understanding of the Sigma1 receptor system remains elusive.

Most prostate cancer patients become unresponsive to initially effective hormone- and chemotherapy, as prostate tumor cells eventually adapt and develop resistance. Treatment with Sigma antagonists leads to apoptotic cell death of both androgen-sensitive and androgen-insensitive prostate cancer cells (Berthosis et al., 2003, Br. J. Cancer 88:438-446; Spruce et al., 2004, Cancer Res. 64:4875-4886). Although some insight has been gained into how prostate cancer cells develop such resistance, currently there are few alternatives to treat hormone refractory (castration resistant) prostate cancer. Emerging therapies to treat intractable, advanced prostate cancers target protein processing and chaperone pathways that maintain prostate tumor growth and survival.

There is a need in the art to identify compounds useful in the treatment of cancers. In certain embodiments, such compounds target at least one selected from the group consisting of protein processing, protein synthesis, protein folding, protein transport, protein localization, protein assembly into functional macromolecular complexes, and/or related chaperone pathways, all of which may help maintain tumor growth, survival and metastasis. The present embodiments described herein fulfill these needs and others.

BRIEF SUMMARY OF THE INVENTION

The invention provides a compound of Formula (I),

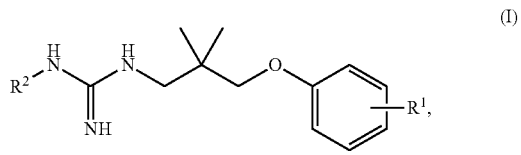

(I)

wherein: $R^1$ is selected from the group consisting of H, halo, and haloalkyl; and $R^2$ is pyrimidinyl, or a pharmaceutically acceptable salt or solvate thereof.

In certain embodiments, the haloalkyl is $C_1$-$C_6$ haloalkyl.

In certain embodiments, $R^1$ is fluoro substituted $C_1$-$C_6$ alkyl.

In certain embodiments, $R^1$ is selected from the group consisting of —$CF_3$, —$C_2F_5$, —$CH_2F$, —$CHF_2$, —$CCl_3$, —$CHCl_2$, and —$CH_2CF_3$.

In certain embodiments, the compound is selected from the group consisting of:

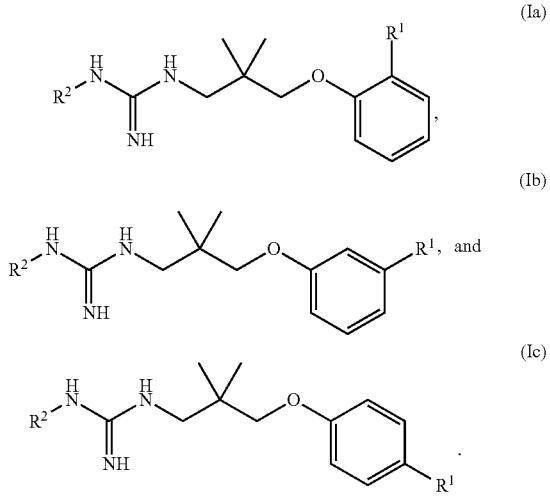

In certain embodiments, $R^2$ is selected from the group consisting of

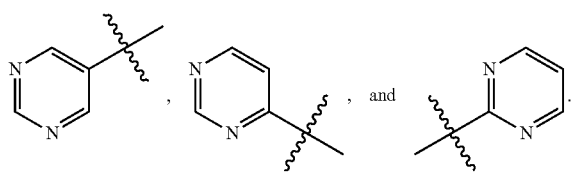 [SMILES: *c1cncnc1 ; *c1ccncn1 ; *c1ncccn1]

In certain embodiments, the compound is

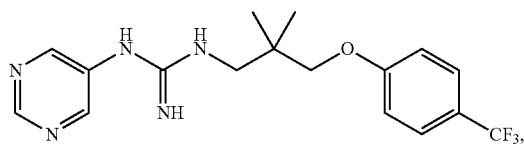

or a pharmaceutically acceptable salt or solvate thereof.

The invention further provides a pharmaceutical composition comprising a compound of the invention, or a pharmaceutically acceptable salt or solvate thereof.

In certain embodiments, the composition further comprises at least one additional therapeutic agent that inhibits the ubiquitin proteasome system (UPS) or autophagic survival pathway.

The invention further provides a method of treating and/or preventing cancer in a mammal.

The invention further provides a method of treating and/or preventing pain. In certain embodiments, the invention provides a method of treating and/or preventing neuropathic pain.

The invention further provides a method of treating and/or preventing a neurological disease, such as but not limited to depression, cocaine abuse, epilepsy, psychosis, Alzheimer's Disease, Parkinson's Disease, Amyotrophic lateral sclerosis (ALS), and Frontotemporal Lobar Degeneration (FTLD). In certain embodiments, the invention provides a method of treating and/or preventing depression. In other embodiments, the invention provides a method of treating and/or preventing cocaine abuse. In yet other embodiments, the invention provides a method of treating and/or preventing epilepsy. In yet other embodiments, the invention provides a method of treating and/or preventing psychosis. In yet other embodiments, the invention provides a method of treating and/or preventing Alzheimer's Disease. In yet other embodiments, the invention provides a method of treating and/or preventing Parkinson's Disease. In yet other embodiments, the invention provides a method of treating and/or preventing Amyotrophic lateral sclerosis (ALS). In yet other embodiments, the invention provides a method of treating and/or preventing Frontotemporal Lobar Degeneration (FTLD).

In certain embodiments, the method comprises administering to the mammal a therapeutically effective amount of a compound of the invention, or a pharmaceutically acceptable salt or solvate thereof.

In certain embodiments, the cancer is at least one selected from the group consisting of lung cancer, prostate cancer, liver cancer, pancreas cancer, CNS tumors, breast cancer, neuroblastoma, and leukemia.

In certain embodiments, the mammal is a mammal in need thereof. In other embodiments, the mammal is a human.

DETAILED DESCRIPTION OF THE INVENTION

Definitions

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "alkyl" means a saturated hydrocarbon group, which can be straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2,2-dimethyl-1-butyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "substituted alkyl" means alkyl as defined above, substituted by one, two or three substituents selected from the group consisting of halogen, —OH, alkoxy, —NH$_2$, —N(CH$_3$)$_2$, —C(=O)OH, trifluoromethyl, —C≡N, —C(=O)O(C$_1$-C$_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "animal" includes, but is not limited to, humans and non-human vertebrates, such as wild, domestic, and farm animals.

As used herein, the phrase "anti-receptor effective amount" of a compound can be measured by the anti-receptor effectiveness of the compound. In certain embodiments, an anti-receptor effective amount inhibits an activity of the receptor by at least 10%, by at least 20%, by at least 30%, by at least 40%, by at least 50%, by at least 60%, by at least 70%, by at least 80%, by at least 90%, or by at least 95%. In certain embodiments, an "anti-receptor effective amount" is also a "therapeutically effective amount," whereby the compound reduces or eliminates at least one effect of a Sigma1 receptor.

As used herein, the term "cancer" means a spectrum of pathological symptoms associated with the initiation or progression, as well as metastasis, of malignant tumors.

As used herein, the term, "compound" means all stereoisomers, tautomers, and isotopes of the compounds described herein.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "contacting" means bringing together of two elements in an in vitro system or an in vivo system. For example, "contacting" a Sigma1 compound with a Sigma1 receptor with an individual or patient or cell includes the administration of the compound to an individual or patient, such as a human, as well as, for example, introducing a compound into a sample containing a cellular or purified preparation containing the Sigma1 receptor.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "halo" means halogen groups including, but not limited to fluoro, chloro, bromo, and iodo.

As used herein, the term "haloalkyl" means a C$_{1-6}$ alkyl group having one or more halogen substituents. Examples of haloalkyl groups include, but are not limited to, CF$_3$, C$_2$F$_5$, CH$_2$F, CHF$_2$, CCl$_3$, CHCl$_2$, CH$_2$CF$_3$, and the like.

As used herein, the term "hydroxy" or "hydroxyl" means an —OH group.

As used herein, the term "hydroxyalkyl" or "hydroxylalkyl" means an alkyl group substituted by at least one hydroxyl group. Examples of a hydroxylalkyl include, but are not limited to, —CH$_2$OH and —CH$_2$CH$_2$OH.

As used herein, the phrase "inhibiting activity," such as enzymatic or receptor activity means reducing by any measurable amount the activity of an enzyme or receptor, such as the Sigma1 receptor.

As used herein, the phrase "in need thereof" means that the animal or mammal has been identified as having a need for the particular method or treatment. In certain embodiments, the identification can be by any means of diagnosis. In any of the methods and treatments described herein, the animal or mammal can be in need thereof. In certain embodiments, the animal or mammal is in an environment or will be traveling to an environment in which a particular disease, disorder, or condition is prevelant.

As used herein, the phrase "integer from X to Y" means any integer that includes the endpoints. For example, the phrase "integer from 1 to 5" means 1, 2, 3, 4, or 5.

As used herein, the term "mammal" means a rodent (e.g., a mouse, a rat, or a guinea pig), a monkey, a cat, a dog, a cow, a horse, a pig, or a human. In certain embodiments, the mammal is a human.

As used herein, the phrase "ophthalmically acceptable" means having no persistent detrimental effect on the treated eye or the functioning thereof, or on the general health of the subject being treated. However, it will be recognized that transient effects such as minor irritation or a "stinging" sensation are common with topical ophthalmic administration of drugs and the existence of such transient effects is not inconsistent with the composition, formulation, or ingredient (e.g., excipient) in question being "ophthalmically acceptable" as herein defined.

The terms "patient," "subject," "individual," and the like are used interchangeably herein, and refer to any animal, or cells thereof whether in vitro or in situ, amenable to the methods described herein. In certain embodiments, a patient, subject, or individual is any animal, including mammals, such as mice, rats, other rodents, rabbits, dogs, cats, swine, cattle, sheep, horses, or primates, such as humans. In a non-limiting embodiment, the patient, subject, or individual is a human.

As used herein, the phrase "pharmaceutically acceptable" means those compounds, materials, compositions, and/or dosage forms which are, within the scope of sound medical judgment, suitable for use in contact with tissues of humans and animals. In certain embodiments, "pharmaceutically acceptable" means approved by a regulatory agency of the Federal or a state government or listed in the U.S. Pharmacopeia or other generally recognized pharmacopeia for use in animals, and more particularly in humans.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

In certain embodiments, the salt of a compound described herein is a "pharmaceutically acceptable salt" thereof. As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfate, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present invention also includes quaternary ammonium salts of the compounds described herein, where the compounds have one or more tertiary amine moiety.

As used herein, the term "prodrug" means a derivative of a known direct acting drug, which derivative has enhanced delivery characteristics and therapeutic value as compared to the drug, and is transformed into the active drug by an enzymatic or chemical process. The compounds, or pharmaceutically acceptable salts thereof, described herein can also be delivered as prodrugs.

As used herein, the term "Sigma" refers to the Sigma1 receptor (Sigma1), Sigma2 receptor (Sigma2), any splice variant thereof or any isoform thereof.

As used herein, a "Sigma receptor modulator" is a compound that binds to the Sigma receptor and modifies the activity or biological function of the receptor as compared to the activity or biological function of the receptor in the absence of the modulator. The modulator may be a receptor agonist, which is able to activate the receptor and cause a biological response that is enhanced over the baseline activity of the unbound receptor. The modulator may be a partial agonist, which does not activate the receptor thoroughly and causes a biological response that is smaller in magnitude compared to those of full agonists. The modulator may be a receptor antagonist, which binds to the receptor but does not activate it, resulting in receptor blockage and inhibiting the binding of other agonists. An antagonist does not diminish the baseline intracellular response in the absence of an agonist. The modulator may be an inverse agonistic, which reduces the activity of the receptor by inhibiting its constitutive activity.

As used herein, the phrase "solubilizing agent" means any agent that can be used to form a micellar solution or a true solution of the drug.

As used herein, the term "solution/suspension" means a liquid composition wherein a first portion of the active agent is present in solution and a second portion of the active agent is present in particulate form, in suspension in a liquid matrix.

A "therapeutic" treatment is a treatment administered to a subject who exhibits signs of pathology, for the purpose of diminishing or eliminating those signs.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. It is specifically intended that embodiments include each and every individual subcombination of the members of such groups and ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. At various places in the present specification, substituents of compounds may be disclosed in groups or in ranges. For example, the term "$C_{1-6}$ alkyl" is specifically intended to individually disclose methyl, ethyl, propyl, $C_4$ alkyl, $C_5$ alkyl, and $C_6$ alkyl.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable subcombination.

Compounds and Compositions

The invention provides certain compounds and salts thereof, as recited herein. Where a variable is not specifically recited, the variable can be any option described herein, except as otherwise noted or dictated by context.

In certain embodiments, the invention provides a compound of Formula (I), or pharmaceutically acceptable salt or solvate thereof:

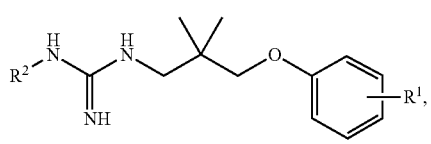

(I)

wherein:
is selected from the group consisting of H, halo, and haloalkyl; and
$R^2$ is pyrimidinyl.

In certain embodiments, the haloalkyl is $C_1$-$C_6$ haloalkyl.

In certain embodiments, $R^1$ is H. In certain embodiments, $R^1$ is halo. In certain embodiments, $R^1$ is haloalkyl.

In certain embodiments, the compound is selected from the group consisting of:

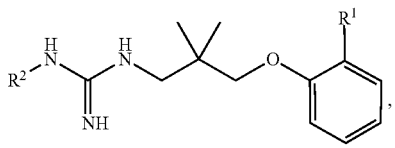

(Ia)

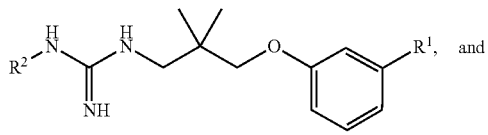

(Ib)

and

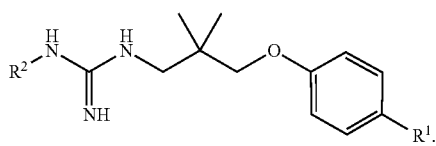

(Ic)

In certain embodiments, $R^1$ is a fluoro substituted $C_1$-$C_6$ alkyl. In certain embodiments, $R^1$ is selected from the group consisting of —$CF_3$, —$C_2F_5$, —$CH_2F$, —$CHF_2$, —$CCl_3$, —$CHCl_2$, —$CH_2CF_3$, and the like. In certain embodiments, $R^1$ is —$CF_3$. In certain embodiments, $R^1$ is —$C_2F_5$. In certain embodiments, $R^1$ is —$CH_2F$. In certain embodiments, $R^1$ is —$CHF_2$. In certain embodiments, $R^1$ is —$CCl_3$. In certain embodiments, $R_1$ is —$CHCl_2$. In certain embodiments, $R^1$ is —$CH_2CF_3$. In certain embodiments, $R^1$ is F. In certain embodiments, $R^1$ is Br. In certain embodiments, $R^1$ is Cl. In certain embodiments, $R^1$ is I.

In certain embodiments, $R^2$ is

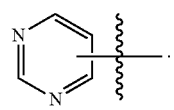

In certain embodiments, $R^2$ is

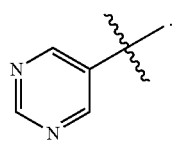

In certain embodiments, $R^2$ is

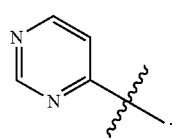

In certain embodiments, $R^2$ is

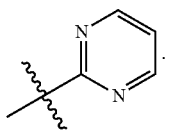

In certain embodiments, the compound is

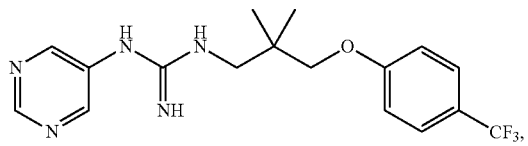 [SMILES: CC(C)(CNC(=N)Nc1cncnc1)COc1ccc(C(F)(F)F)cc1]

or a pharmaceutically acceptable salt or solvate thereof.

The compounds described herein can be asymmetric (e.g., having one or more stereocenters). All stereoisomers, such as enantiomers and diastereomers, are intended to be included within the scope of the invention unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds are also included within the scope of the invention and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, chiral HPLC, fractional recrystallization using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

For example, isotopes of hydrogen include tritium and deuterium. In certain embodiments, the hydrogens of the methyl groups can be substituted with deuterium.

In certain embodiments, the compounds, or salts or solvate thereof, are substantially isolated. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound, or salt thereof. Methods for isolating compounds and their salts are routine in the art.

The compounds also include derivatives referred to as prodrugs.

It is understood that the present embodiments encompasses the use, where applicable, of stereoisomers, diastereomers and optical stereoisomers of the compounds of the invention, as well as mixtures thereof Additionally, it is understood that stereoisomers, diastereomers, and optical stereoisomers of the compounds of the invention, and mixtures thereof, are within the scope of the invention. By way of non-limiting example, the mixture can be a racemate or the mixture may comprise unequal proportions of one particular stereoisomer over the other. Additionally, the compounds can be provided as a substantially pure stereoisomers, diastereomers and optical stereoisomers (such as epimers).

In certain embodiments, the present invention provides pharmaceutical compositions comprising any compound described herein, or pharmaceutically salt or solvate thereof.

The compounds described herein can be made by can be made according to the methods described herein and in the examples. The methods described herein can be adapted based upon the compounds desired and described herein. In certain embodiments, this method can be used to make one or more compounds as described herein and will be apparent to one of skill in the art which compounds can be made according to the methods described herein.

The conditions and temperatures can be varied, such as shown in the examples described herein. These schemes are non-limiting synthetic schemes and the synthetic routes can be modified as would be apparent to one of skill in the art reading the present specification. The compounds can also be prepared according to the schemes described in the Examples and by, for example, varying the starting materials and intermediates shown, for example, in Example 1.

In certain embodiments, the compounds of the invention can be used to modulate the Sigma1 receptor. Thus, in certain embodiments, the compounds can be referred to as Sigma1 receptor modulating compounds.

Methods

In certain embodiments, the invention provides a method of treating and/or preventing cancer in a mammal. In other embodiments, the method comprises administering to the mammal at least one compound of the invention, and/or a pharmaceutically acceptable salt or solvate thereof, and/or a pharmaceutical composition thereof.

In certain embodiments, the invention provides a method of treating and/or preventing pain.

In certain embodiments, the invention provides a method of treating and/or preventing a neurological disease.

In certain embodiments, the invention provides a method of treating, ameliorating or preventing a Sigma receptor-related disorder or disease in a subject. The method comprises administering to the subject an effective amount of a compound of the invention, or a pharmaceutically acceptable salt or solvate thereof, and further administering to the subject a therapeutic agent that inhibits the ubiquitin proteasome system (UPS) and/or autophagic survival pathways.

In certain embodiments, administering the compound of the invention to the subject allows for administering a lower dose of the therapeutic agent that inhibits the ubiquitin proteasome system (UPS) and/or autophagic survival pathways, as compared to the dose of the therapeutic agent alone that is required to achieve similar results in treating, ameliorating or preventing the Sigma receptor-related disorder in the subject. In another embodiment, the compound of the invention and the therapeutic agent are co-administered to the subject. In yet another embodiment, the compound of the invention and the therapeutic agent are co-formulated and co-administered to the subject.

In one embodiment, the methods described herein further comprise inhibiting the Sigma receptor. In another embodiment, the methods described herein further comprise modulating the Sigma receptor.

In certain embodiments, the mammal is a mammal in need thereof. In other embodiments, the mammal is human. In yet other embodiments, the cancer is at least one selected from the group consisting of lung cancer, prostate cancer, liver cancer, pancreas cancer, CNS tumors, breast cancer, neuroblastoma, leukemia.

In certain embodiments, the cancer is lung cancer. In other embodiments, the cancer is prostate cancer. In yet other embodiments, the cancer is liver cancer. In yet other embodiments, the cancer is pancreas cancer. In yet other embodiments, the cancer is a CNS tumor. In yet other embodiments, the cancer is breast cancer. In yet other embodiments, the cancer is neuroblastoma. In yet other embodiments, the cancer is leukemia.

Combination Therapies

The compounds of the present invention are intended to be useful in combination with one or more additional compounds. These additional compounds may comprise compounds of the present invention or therapeutic agents known to treat, prevent, or reduce the symptoms or effects of Sigma receptor-related disorders or diseases. Such compounds include, but are not limited to, hormone receptor antagonists, autophagy inhibitors, ER stress response inhibitors, and proteasome inhibitors.

In non-limiting examples, the compounds of the invention may be used in combination with one or more therapeutic agents (or a salt, solvate or prodrug thereof) selected from the group consisting of
    hormone receptor antagonists, including but are not limited to octapeptide, somatostatin, analoguem, lanreotide, angiopeptin, dermopeptin, octreotide, and pegvisomant;
    autophagy inhibitors, including but are not limited to 3-methyladenine, chloroquine, hydroxychloroquine, and wortmannin;
    ER stress response inhibitors, including but are not limited to eeyarestatin I, salubrinal, and versipelostatin;
    proteasome inhibitors, including but are not limited to 2H-isoindole-2-carboxylic acid, 4-fluoro-1,3-dihydro-(2R,6S,12Z,13aS,14aR,16aS)-14a-[[(cyclopropylsulfonyl)amino]carbonyl]-6-[[(1,1-dimethylethoxy)carbonyl]amino]-1,2,3,5,6,7,8,9,10,11,13a,14,14a,15,16,16a-hexadecahydro-5,16-dioxocyclopropa[e]pyrrolo[1,2-a][1,4]diazacyclopentadecin-2-yl ester (Danoprevir), adamantane-acetyl-(6-aminohexanoyl)3-(leucinyl)3-vinyl-(methyl)-sulfone, N-acetyl-L-leucyl-L-leucyl-L-methional, N-[(phenylmethoxy)carbonyl]-L-leucyl-N-[(1S)-1-formyl-3-methylbutyl]-L-leucinamide, (2R,3S,4R)-3-hydroxy-2-[(1S)-1-hydroxy-2-methylpropyl]-4-methyl-5-oxo-2-pyrrolidinecarboxy-N-acetyl-L-cysteine thioester, N-[N-(N-acetyl-L-leucyl)-L-leucyl]-L-norleucine, lactacystin, 4-(2-aminoethyl)benzenesulfonyl fluoride hydrochloride, (S)-1-carboxy-2-phenyl]-carbamoyl-arg-val-arginal, bovine pancreatic trypsin inhibitor, [(2S, 2R)-3-amino-2-hydroxy-4-phenylbutanoyl]-L-leucine, N-[(S)-1-carboxy-isopentyl)-carbamoyl-alpha-(2-iminohexahydro-4-(S)-pyrimidyl]-L-glycyl-L-phenylalaninal, ethylenediamine-tetraacetic acid disodium salt dehydrate, acetyl-leucyl-leucyl-arginal, isovaleryl-val-val-AHMHA-ala-AHMHA where AHMHA=(3S, 4S)-4-amino-3-hydroxy-6-methylheptanoic acid, N-alpha-L-rhamnopyranosyloxy(hydroxyphosphinyl)-L-leucyl-L-tryptophan, phenylmethanesulfonyl fluoride, bortezomib, carfilzomib, ONX 0912, NPI-0052, CEP-18770, MLN9708, disulfiram, epigallocatechin-3-gallate, and salinosporamide A; and
    p97/VCP inhibitors, including but not limited to DBeQ and derivatives thereof.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The compounds described herein can be administered in any conventional manner by any route where they are active.

Administration can be systemic, topical, or oral. For example, administration can be, but is not limited to, parenteral, subcutaneous, intravenous, intramuscular, intraperitoneal, transdermal, oral, buccal, sublingual, or ocular routes, or intravaginally, by inhalation, by depot injections, or by implants. The mode of administration can depend on the conditions or disease to be targeted or treated. The selection of the specific route of administration can be selected or adjusted by the clinician according to methods known to the clinician to obtain the desired clinical response.

In certain embodiments, it may be desirable to administer one or more compounds, or a pharmaceutically acceptable salt thereof, locally to an area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, wherein the implant is of a porous, non-porous, or gelatinous material, including membranes, such as sialastic membranes, or fibers.

The compounds described herein can be administered either alone or in combination (concurrently or serially) with other pharmaceuticals. For example, the compounds can be administered in combination with other chemotherapeutics or drugs used to treat cancer.

The means and methods for administration are known in the art and an artisan can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The standard dosing for protamine can be used and adjusted (i.e., increased or decreased) depending upon the factors described above. The selection of the specific dose regimen can be selected or adjusted or titrated by the clinician according to methods known to the clinician to obtain the desired clinical response.

The amount of a compound described herein that will be effective in the treatment and/or prevention of a particular disease, condition, or disorder will depend on the nature and extent of the disease, condition, or disorder, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In certain embodiments, the oral dose is about 5 milligrams per kilogram body weight.

In certain embodiments, suitable dosage ranges for intravenous (i.v.) administration are from about 0.01 mg to about 500 mg per kg body weight, from about 0.1 mg to about 100 mg per kg body weight, from about 1 mg to about 50 mg per kg body weight, or from about 10 mg to about 35 mg per kg body weight. Suitable dosage ranges for other modes of administration can be calculated based on the forgoing dosages as known by those skilled in the art. For example, recommended dosages for intranasal, transmucosal, intradermal, intramuscular, intraperitoneal, subcutaneous, epidural, sublingual, intracerebral, intravaginal, transdermal administration or administration by inhalation are in the range of from about 0.001 mg to about 200 mg per kg of body weight, from about 0.01 mg to about 100 mg per kg of body weight, from about 0.1 mg to about 50 mg per kg of body weight, or from about 1 mg to about 20 mg per kg of body weight. Effective doses may be extrapolated from dose-response curves derived from in vitro or animal model test systems. Such animal models and systems are well known in the art.

The compounds described herein can be formulated for parenteral administration by injection, such as by bolus injection or continuous infusion. The compounds can be administered by continuous infusion subcutaneously over a period of about 15 minutes to about 24 hours. Formulations for injection can be presented in unit dosage form, such as in ampoules or in multi-dose containers, with an optionally added preservative. The compositions can take such forms as suspensions, solutions or emulsions in oily or aqueous vehicles, and can contain formulatory agents such as suspending, stabilizing and/or dispersing agents. In certain embodiments, the injectable is in the form of short-acting, depot, or implant and pellet forms injected subcutaneously or intramuscularly. In certain embodiments, the parenteral dosage form is the form of a solution, suspension, emulsion, or dry powder.

For oral administration, the compounds described herein can be formulated by combining the compounds with pharmaceutically acceptable carriers well known in the art. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

For administration by inhalation, the compounds described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compounds described herein can also be formulated in rectal compositions such as suppositories or retention enemas, such as containing conventional suppository bases such as cocoa butter or other glycerides. The compounds described herein can also be formulated in vaginal compositions such as vaginal creams, suppositories, pessaries, vaginal rings, and intrauterine devices.

In transdermal administration, the compounds can be applied to a plaster, or can be applied by transdermal, therapeutic systems that are consequently supplied to the organism. In certain embodiments, the compounds are present in creams, solutions, powders, fluid emulsions, fluid suspensions, semi-solids, ointments, pastes, gels, jellies, and foams, or in patches containing any of the same.

The compounds described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In certain embodiments, the compounds can be delivered in a controlled release system. In one embodiment, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574).

In one embodiment, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

It is also known in the art that the compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In certain embodiments, the compounds described herein can be used with agents including, but not limited to, topical analgesics (e.g., lidocaine), barrier devices (e.g., GelClair), or rinses (e.g., Caphosol).

In certain embodiments, the compounds described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

Suitable compositions include, but are not limited to, oral non-absorbed compositions. Suitable compositions also include, but are not limited to saline, water, cyclodextrin solutions, and buffered solutions of pH 3-9.

The compounds described herein, or pharmaceutically acceptable salts thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)aminomethane HCl (pH7.0), 0.9% saline, and 1.2% saline, and any combination thereof. In certain embodiments, excipient is chosen from propylene glycol, purified water, and glycerin.

In certain embodiments, the formulation can be lyophilized to a solid and reconstituted with, for example, water prior to use.

When administered to a mammal (e.g., to an animal for veterinary use or to a human for clinical use) the compounds can be administered in isolated form.

When administered to a human, the compounds can be sterile. Water is a suitable carrier when the compound of Formula I is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A. R. Gennaro (Editor) Mack Publishing Co.

In certain embodiments, the compounds are formulated in accordance with routine procedures as a pharmaceutical composition adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In certain embodiments, a composition of the present invention is in the form of a liquid wherein the active agent (i.e., one of the facially amphiphilic polymers or oligomers disclosed herein) is present in solution, in suspension, as an emulsion, or as a solution/suspension. In certain embodiments, the liquid composition is in the form of a gel. In other embodiments, the liquid composition is aqueous. In other embodiments, the composition is in the form of an ointment.

In certain embodiments, the composition is in the form of a solid article. For example, in certain embodiments, the ophthalmic composition is a solid article that can be inserted in a suitable location in the eye, such as between the eye and eyelid or in the conjunctival sac, where it releases the active agent as described, for example, U.S. Pat. Nos. 3,863,633; 3,867,519; 3,868,445; 3,960,150; 3,963,025; 4,186,184; 4,303,637; 5,443,505; and 5,869,079. Release from such an article is usually to the cornea, either via the lacrimal fluid that bathes the surface of the cornea, or directly to the cornea itself, with which the solid article is generally in intimate contact. Solid articles suitable for implantation in the eye in such fashion are generally composed primarily of polymers and can be bioerodible or non-bioerodible. Bioerodible polymers that can be used in the preparation of ocular implants carrying one or more of the anti-microbial, facially amphiphilic polymer or oligomer active agents in accordance with the present invention include, but are not limited to, aliphatic polyesters such as polymers and copolymers of poly(glycolide), poly(lactide), poly(epsilon-caprolactone), poly-(hydroxybutyrate) and poly(hydroxyvalerate), polyamino acids, polyorthoesters, polyanhydrides, aliphatic polycarbonates and polyether lactones. Suitable non-bioerodible polymers include silicone elastomers.

The compositions described herein can contain preservatives. Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfate, acetylcysteine, polyquaternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

In certain embodiments, the compounds are solubilized at least in part by an acceptable solubilizing agent. Certain acceptable nonionic surfactants, for example polysorbate 80, can be useful as solubilizing agents, as can ophthalmically acceptable glycols, polyglycols, e.g., polyethylene glycol 400 (PEG-400), and glycol ethers.

Suitable solubilizing agents for solution and solution/suspension compositions are cyclodextrins. Suitable cyclodextrins can be chosen from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like. Ophthalmic applications of cyclodextrins have been reviewed in Rajewski et al., Journal of Pharmaceutical Sciences, 1996, 85, 1155-1159.

In certain embodiments, the composition optionally contains a suspending agent. For example, in those embodiments in which the composition is an aqueous suspension or solution/suspension, the composition can contain one or more polymers as suspending agents. Useful polymers include, but are not limited to, water-soluble polymers such as cellulosic polymers, for example, hydroxypropyl methylcellulose, and water-insoluble polymers such as cross-linked carboxyl-containing polymers.

One or more acceptable pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

One or more acceptable salts can be included in the compositions of the invention in an amount required to bring osmolality of the composition into an acceptable range. Such salts include, but are not limited to, those having sodium, potassium or ammonium cations and chloride, citrate, ascorbate, borate, phosphate, bicarbonate, sulfate, thiosulfate or bisulfite anions. In certain embodiments, salts include sodium chloride, potassium chloride, sodium thiosulfate, sodium bisulfite and ammonium sulfate. In certain embodiments, the salt is sodium chloride.

Optionally one or more acceptable surfactants, preferably nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., PLURONIC® F-68, F84 and P-103); cyclodextrin; or other agents known to those of skill in the art. Typically, such co-solvents or surfactants are employed in the compositions at a level of from about 0.01% to about 2% by weight.

The present invention also provides pharmaceutical packs or kits comprising one or more containers filled with one or more compounds described herein. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In certain embodiments, the kit contains more than one compound described herein. In certain embodiments, the kit comprises a compound described herein in a single injectable dosage form, such as a single dose within an injectable device such as a syringe with a needle.

Those skilled in the art recognizes, or is able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

In certain aspects, the present invention provides embodiments including, but are not limited to:

Embodiment 1: A compound of Formula (I),

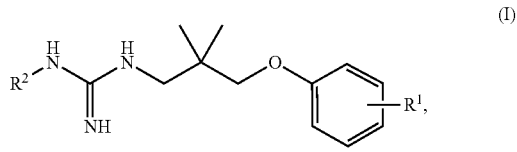

wherein: $R^1$ is selected from the group consisting of H, halo, and haloalkyl; and $R^2$ is pyrimidinyl, or a pharmaceutically acceptable salt or solvate thereof.

Embodiment 2: The compound of Embodiment 1, wherein the haloalkyl is $C_1$-$C_6$ haloalkyl.

Embodiment 3: The compound of any of Embodiments 1-2, wherein $R^1$ is fluoro substituted $C_1$-$C_6$ alkyl.

Embodiment 4: The compound of any of Embodiments 1-3, wherein $R^1$ is selected from the group consisting of —$CF_3$, —$C_2F_5$, —$CH_2F$, —$CHF_2$, —$CCl_3$, —$CHCl_2$, and —$CH_2CF_3$.

Embodiment 5: The compound of any of Embodiments 1-4, which is selected from the group consisting of:

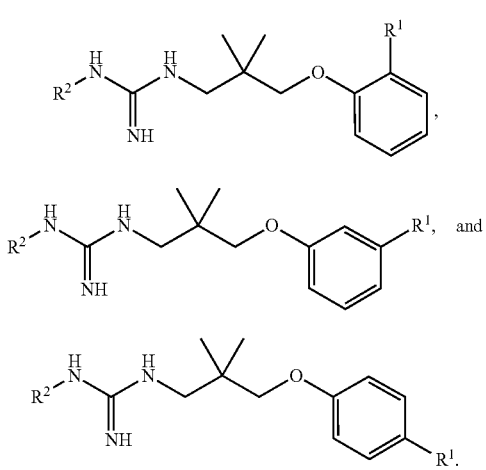

Embodiment 6: The compound of any of Embodiments 1-5, wherein $R^2$ is selected from the group consisting of

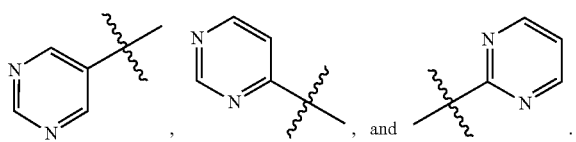 [SMILES: *c1cncnc1 ; *c1ccncn1 ; *c1ncccn1]

Embodiment 7: The compound of any of Embodiments 1-6, which is:

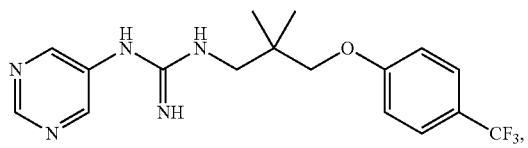 [SMILES: CC(C)(CNC(=N)Nc1cncnc1)COc1ccc(C(F)(F)F)cc1]

or a pharmaceutically acceptable salt or solvate thereof.
Embodiment 8: A pharmaceutical composition comprising a compound of any of Embodiments 1-7, or a pharmaceutically acceptable salt or solvate thereof.
Embodiment 9: The pharmaceutical composition of Embodiment 8, further comprising at least one additional therapeutic agent that inhibits the ubiquitin proteasome system (UPS) or autophagic survival pathway.
Embodiment 10: A method of treating cancer in a mammal, the method comprising administering to the mammal a therapeutically effective amount of a compound of any Embodiments 1-7, or a pharmaceutically acceptable salt or solvate thereof.
Embodiment 11: The method of Embodiment 10, wherein the cancer is at least one selected from the group consisting of lung cancer, prostate cancer, liver cancer, pancreas cancer, CNS tumors, breast cancer, neuroblastoma, and leukemia.
Embodiment 12: The method of any of Embodiments 10-11, wherein the mammal is a mammal in need thereof.
Embodiment 13: The method of any of Embodiments 10-12, wherein the mammal is a human.
Embodiment 14: A method of treating pain, the method comprising administering to the mammal a therapeutically effective amount of a compound of any of Embodiments 1-7, or a pharmaceutically acceptable salt or solvate thereof.
Embodiment 15: The method of Embodiment 14, wherein the mammal is a mammal in need thereof.
Embodiment 16: The method of any of Embodiments 14-15, wherein the mammal is a human.
Embodiment 17: A method of treating a neurological disease, the method comprising administering to the mammal a therapeutically effective amount of any of Embodiments 1-7, or a pharmaceutically acceptable salt or solvate thereof.
Embodiment 18: The method of Embodiment 17, wherein the mammal is a mammal in need thereof.
Embodiment 19: The method of any of Embodiments 17-18, wherein the mammal is a human.

The following examples further illustrate aspects of the present invention. However, they are in no way a limitation of the teachings or disclosure of the present invention as set forth herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Synthesis of 1-(2,2-dimethyl-3-(4-(trifluoromethyl)phenoxy)propyl)-3-(pyrimidin-5-yl) guanidine The compound was made according to the following scheme:

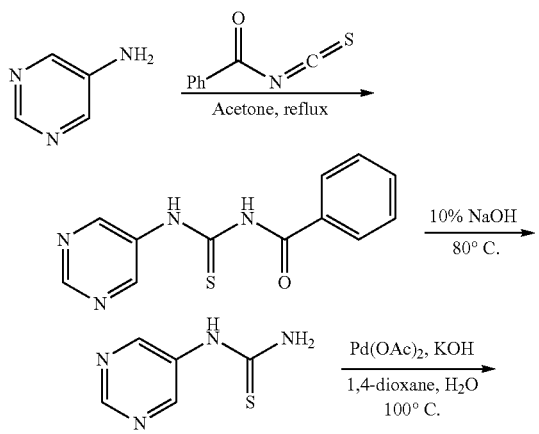

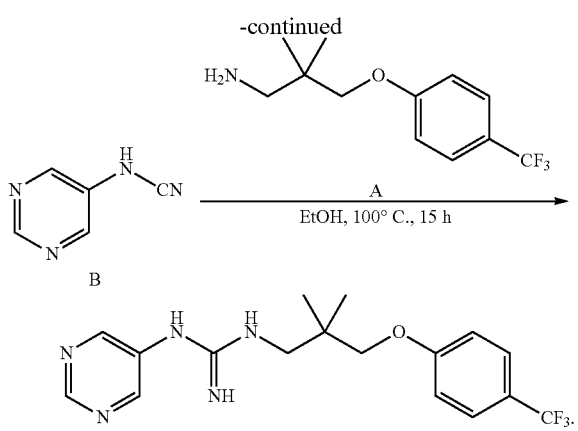

A mixture of A (200 mg, 0.81 mmol) and B (97 mg, 0.81 mmol) in EtOH (4 mL) was stirred under $N_2$ at 100° C. for 15 h. After the reaction was cooled to room temperature, the mixture was concentrated and purified by column chromatography (MeOH:DCM:EA=1:15:15) to afford the compound as a pale-yellow solid. $^1$H NMR (400 MHz, DMSO-$d_6$) δ8.55 (s, 1H), 8.08 (s, 2H), 7.62 (d, J=8.8 Hz, 2H), 7.12 (d, J=8.8 Hz, 2H), 5.82 (t, J=6.0 Hz, 1H), 5.40 (s, 2H), 3.80 (s, 2H), 3.25 (d, J=6.0 Hz, 2H), 1.02 (s, 6H). LCMS: m/z calculated for $C_{17}H_{20}F_3N_5O$: 367.4; found: 368.4 [M+H].

Example 2: Compounds Modulate Sigma1 Receptor Activity 1-(2,2-Dimethyl-3-(4-(trifluoromethyl)phenoxy)propyl)-3-(pyrimidin-5-yl)guanidine was tested for binding to Sigma1 receptor and found to bind to the Sigma1 receptor in the nanomolar range. The compound's activity was also measured for its ability to inhibit androgen receptor reporter activity. The assay that was used was Indigo Biosciences Human Androgen Receptor Reporter Assay System. The compound was found to be active. Based upon these activities, the compounds are expected to have anti-tumor effects.

Example 3: Compounds Treat Cancer 1-(2,2-Dimethyl-3-(4-(trifluoromethyl)phenoxy)propyl)-3-(pyrimidin-5-yl)guanidine is administered to a subject who has breast cancer. The tumor growth is inhibited and the tumor size is reduced.

Example 4: Compounds Treat Cancer 1-(2,2-Dimethyl-3-(4-(trifluoromethyl)phenoxy)propyl)-3-(pyrimidin-5-yl)guanidine is administered to a subject in pain. The subject's pain is alleviated.

The disclosures of each and every patent, patent application, and publication cited herein are hereby incorporated herein by reference in their entirety. While the present invention has been disclosed with reference to specific embodiments, it is apparent that other embodiments and variations of the present invention may be devised by others skilled in the art without departing from the true spirit and scope of the invention. The appended claims are intended to be construed to include all such embodiments and equivalent variations.

What is claimed is:

1. A compound of Formula (I),

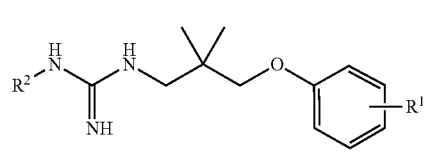

(I)

wherein:
$R^1$ is selected from the group consisting of H, halo, and haloalkyl; and
$R^2$ is pyrimidinyl,
or a pharmaceutically acceptable salt or solvate thereof.

2. The compound of claim 1, wherein the haloalkyl is $C_1$-$C_6$ haloalkyl.

3. The compound of claim 1, wherein $R^1$ is fluoro substituted $C_1$-$C_6$ alkyl.

4. The compound of claim 1, wherein $R^1$ is selected from the group consisting of —$CF_3$, —$C_2F_5$, —$CH_2F$, —$CHF_2$, —$CCl_3$, —$CHCl_2$, and —$CH_2CF_3$.

5. The compound of claim 1, which is selected from the group consisting of:

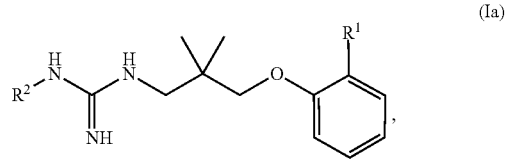

(Ia)

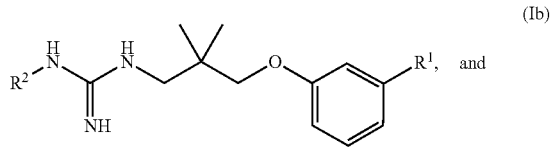

(Ib)

and

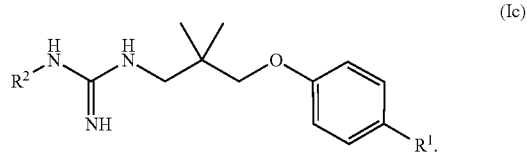

(Ic)

6. The compound of claim 1, wherein $R^2$ is selected from the group consisting of

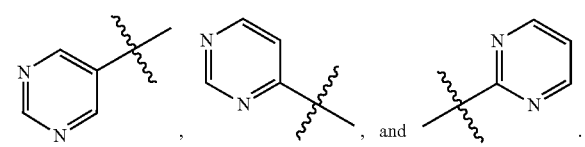 [SMILES: *c1cncnc1 ; *c1ccncn1 ; *c1ncccn1]

7. The compound of claim 1, which is:

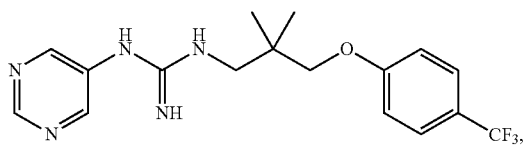

or a pharmaceutically acceptable salt or solvate thereof.

8. A pharmaceutical composition comprising the compound of claim 1, or a pharmaceutically acceptable salt or solvate thereof.

9. The pharmaceutical composition of claim 8, further comprising at least one additional therapeutic agent that inhibits the ubiquitin proteasome system (UPS) or autophagic survival pathway.

* * * * *